US00PP30385P3

(12) United States Plant Patent
Whitaker et al.

(10) Patent No.: US PP30,385 P3
(45) Date of Patent: Apr. 16, 2019

(54) STRAWBERRY PLANT NAMED 'FLORIDA BEAUTY'

(50) Latin Name: ***Fragaria* X *ananassa* Duchesne**
Varietal Denomination: Florida Beauty

(71) Applicants: Florida Foundation Seed Producers, Inc., Marianna, FL (US); State of Queensland acting through The Department of Agriculture and Fisheries, Brisbane QLD (AU)

(72) Inventors: Vance M. Whitaker, Brandon, FL (US); Mark Herrington, Nambour (AU)

(73) Assignee: FLORIDA FOUNDATION SEED PRODUCERS, INC., Marianna, FL (US)

( * ) Notice: Subject to any disclaimer, the term of this patent is extended or adjusted under 35 U.S.C. 154(b) by 0 days.

(21) Appl. No.: 15/530,158

(22) Filed: Dec. 7, 2016

(65) Prior Publication Data

US 2018/0160591 P1 Jun. 7, 2018

(51) Int. Cl.
*A01H 5/08* (2018.01)
*A01H 6/74* (2018.01)

(52) U.S. Cl.
USPC ..... Plt./209
CPC ..... *A01H 6/7409* (2018.05); *A01H 5/08* (2013.01)

(58) Field of Classification Search
USPC ..... Plt./209
See application file for complete search history.

(56) References Cited

U.S. PATENT DOCUMENTS

PP20,363 P2 9/2009 Chandler
PP23,042 P3 9/2012 Chandler
PP25,574 P3 5/2015 Whitaker et al.

*Primary Examiner* — Anne Marie Grunberg
(74) *Attorney, Agent, or Firm* — Dentons US LLP

(57) ABSTRACT

A new and distinct variety of strawberry plant (*Fragaria* X *ananassa*), which originated from seed produced by a hand-pollinated cross between AU 2010-119 and 'Florida Radiance'. The new strawberry plant, named 'Florida Beauty', is distinguished by its compact growth habit; steady yield; fruit that are exceptionally and consistently well-shaped, bright medium-red, and having an exceptional, balanced flavor when grown in west central Florida or other areas that have a subtropical climate similar to that of west central Florida.

5 Drawing Sheets

Latin name of the genus and species of the plant claimed: *Fragaria* X *ananassa* Duchesne.

Variety denomination: 'Florida Beauty'.

BACKGROUND OF THE INVENTION

The present invention relates to a new and distinct variety of strawberry (*Fragaria* X *ananassa* Duchesne) named 'Florida Beauty'. This new strawberry plant is distinguished by its compact growth habit and ability to produce steady yields of fruit that are consistently shaped and have exceptional flavor when grown in west central Florida. Asexual propagation was performed at Balm, Fla. where the selection was made and plants were tested. Contrast is made to 'Florida Radiance' (U.S. Plant Pat. No. 20,363) and 'Florida127' (U.S. Plant Pat. No. 25,574), currently the dominant varieties in Hillsborough County, Fla., for reliable description. This new variety is a promising candidate for commercial success because it can be planted earlier than other varieties due to its compact plant habit and because it produces flavorful fruit that are evenly colored and consistently shaped during the entire Florida market window.

This strawberry plant (genotype) originated in a strawberry breeding plot in Balm, Fla. The seed parent was AU 2010-119, an unreleased breeding selection with the ability to produce fruit with excellent flavor and shape. The pollen parent was 'Florida Radiance' (U.S. Plant Pat. No. 20,363), a strawberry cultivar with high early yields, steady yield pattern, and low vegetative vigor. The seeds resulting from the controlled hybridization were germinated in a greenhouse, and the resulting seedlings were planted and allowed to produce daughter plants by asexual propagation (i.e. by runners). Two daughter plants from each seedling were transplanted to raised beds, where they fruited. 'Florida Beauty' (as represented by two daughter plants from the original seedling) exhibited compact plant habit and steady yields of consistently shaped fruit, and therefore was selected for further evaluation. 'Florida Beauty' was selection number 5 of the 121$^{st}$ cross in the 2012-2013 seedling trial, and thus was given the breeding trial designation of FL 12.121-5. 'Florida Beauty' has been asexually propagated annually by runners, and further test plantings have established that the vegetative and fruit characteristics of the propagules are identical to the initial daughter plants.

SUMMARY OF THE INVENTION

'Florida Beauty', when grown in a subtropical fall and winter climate, is set apart from all other strawberry plants by a combination of the following characteristics: compact growth habit; steady yield; and fruit that are exceptionally and consistently well-shaped, bright medium-red, and have an exceptional balanced flavor.

'Florida Beauty' plants can be unambiguously distinguished from plants of its seed parent AU 2010-119. For instance, the size of the fruit produced by 'Florida Beauty' plants is less variable over the entire fruiting season than the size of the fruit produced by AU 2010-119 plants. Further, during the period of fruit development and ripening, the petals of 'Florida Beauty' plants are shed more quickly than those of plants AU 2010-119 plants. By shedding its petals sooner, less moisture is trapped on the surface of the fruit produced by 'Florida Beauty' plants than the fruit produced by AU 2010-119 plants.

BRIEF DESCRIPTION OF THE DRAWINGS

The new strawberry plant is illustrated by the accompanying photographs.

FIG. 1—Shows whole plants, including leaves, inflorescences, and fruit at varying stages of ripeness.

FIG. 2—Shows a close-up of the underside of an inflorescence.

FIG. 3—Shows a close-up of a fruit that was produced by a plant of the claimed variety that was grown under summer greenhouse conditions.

FIG. 4—Shows a close-up of a transverse cross section of a fruit that was produced by a plant of the claimed variety that was grown under summer greenhouse conditions.

FIG. 5—Shows a close-up of a longitudinal cross section of a fruit that was produced by a plant of the claimed variety that was grown under summer greenhouse conditions.

DETAILED BOTANICAL DESCRIPTION

Figure 1:
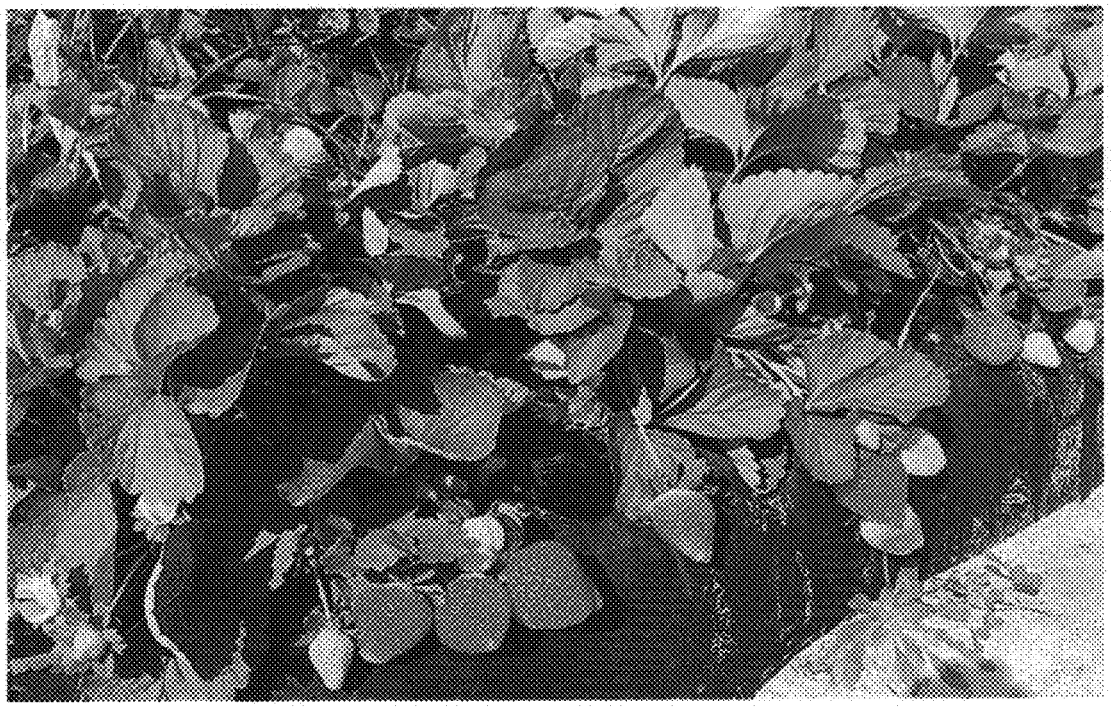
FIG. 1 shows a typical specimen of a 5-month-old plant and fruit as seen in February, 2016, in west central Florida.
Figure 2:
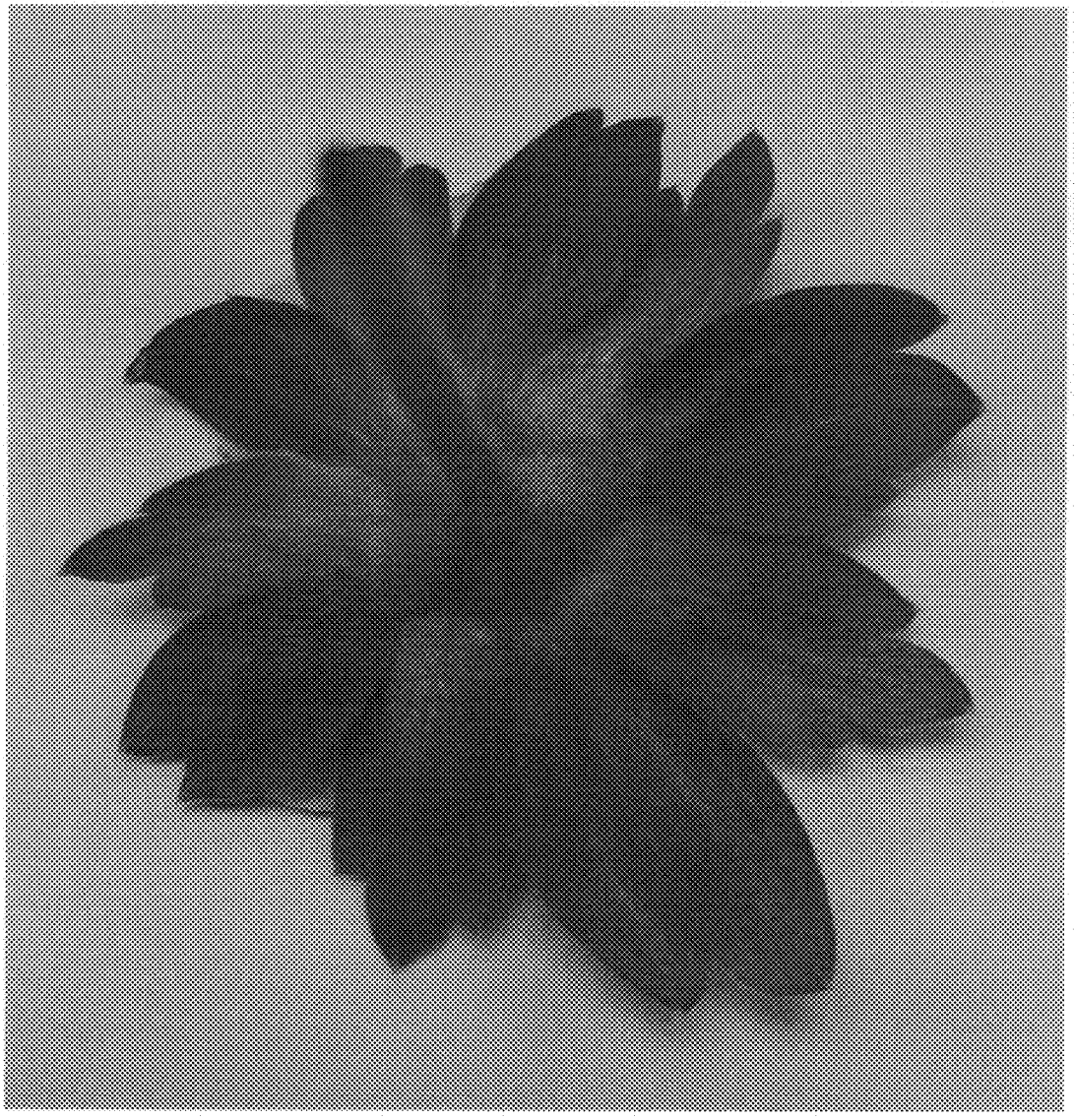
FIGS. 2-5 show typical inflorescence and fruit specimens that were produced by plants of the claimed variety that were grown under summer greenhouse conditions that were significantly warmer than growth conditions in west central Florida during the optimum October through mid-March fruit production window of 'Florida Beauty'. The colors shown are as true as can be reasonably obtained by conventional photographic procedures.
Figure 3:
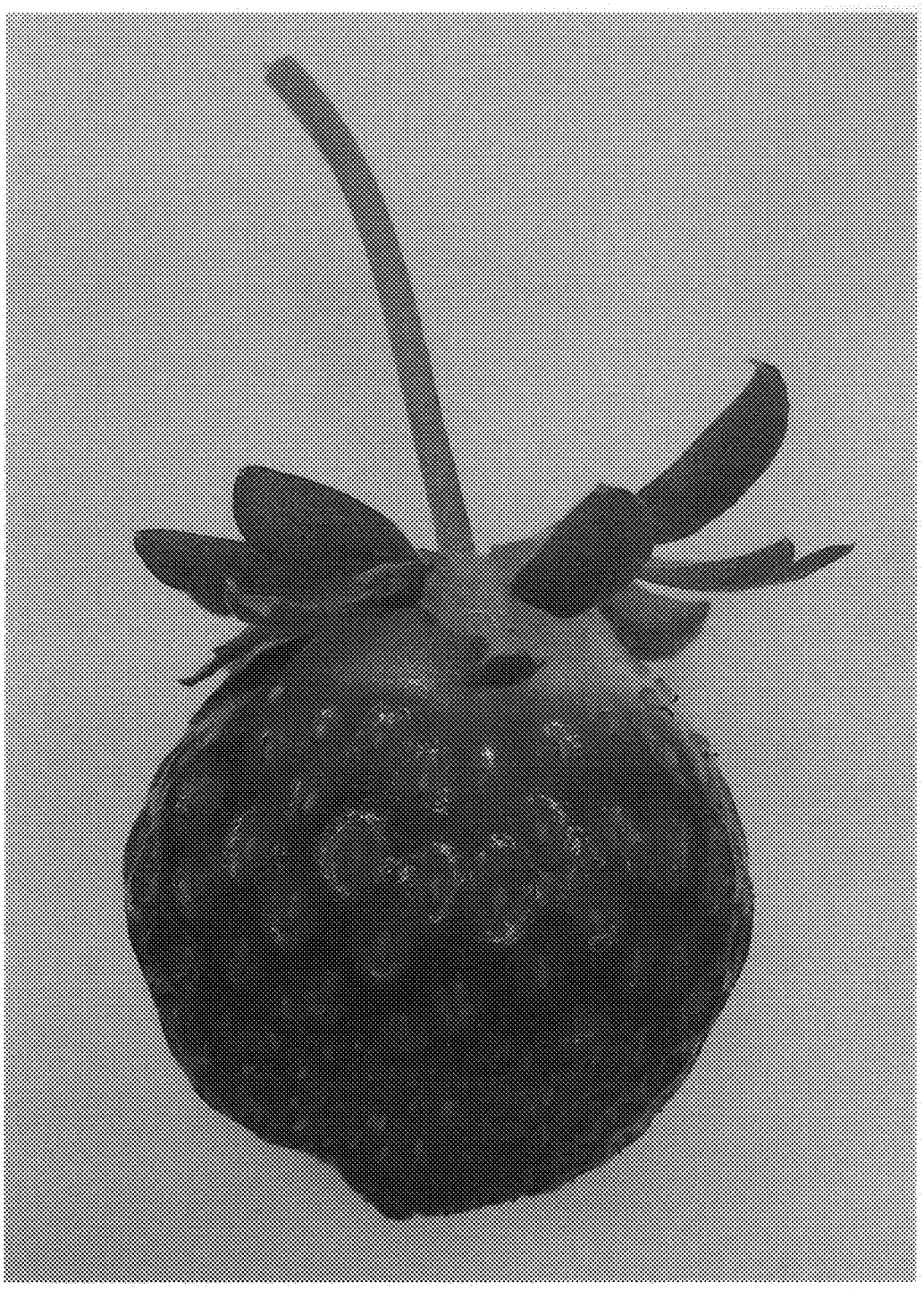
Figure 4:
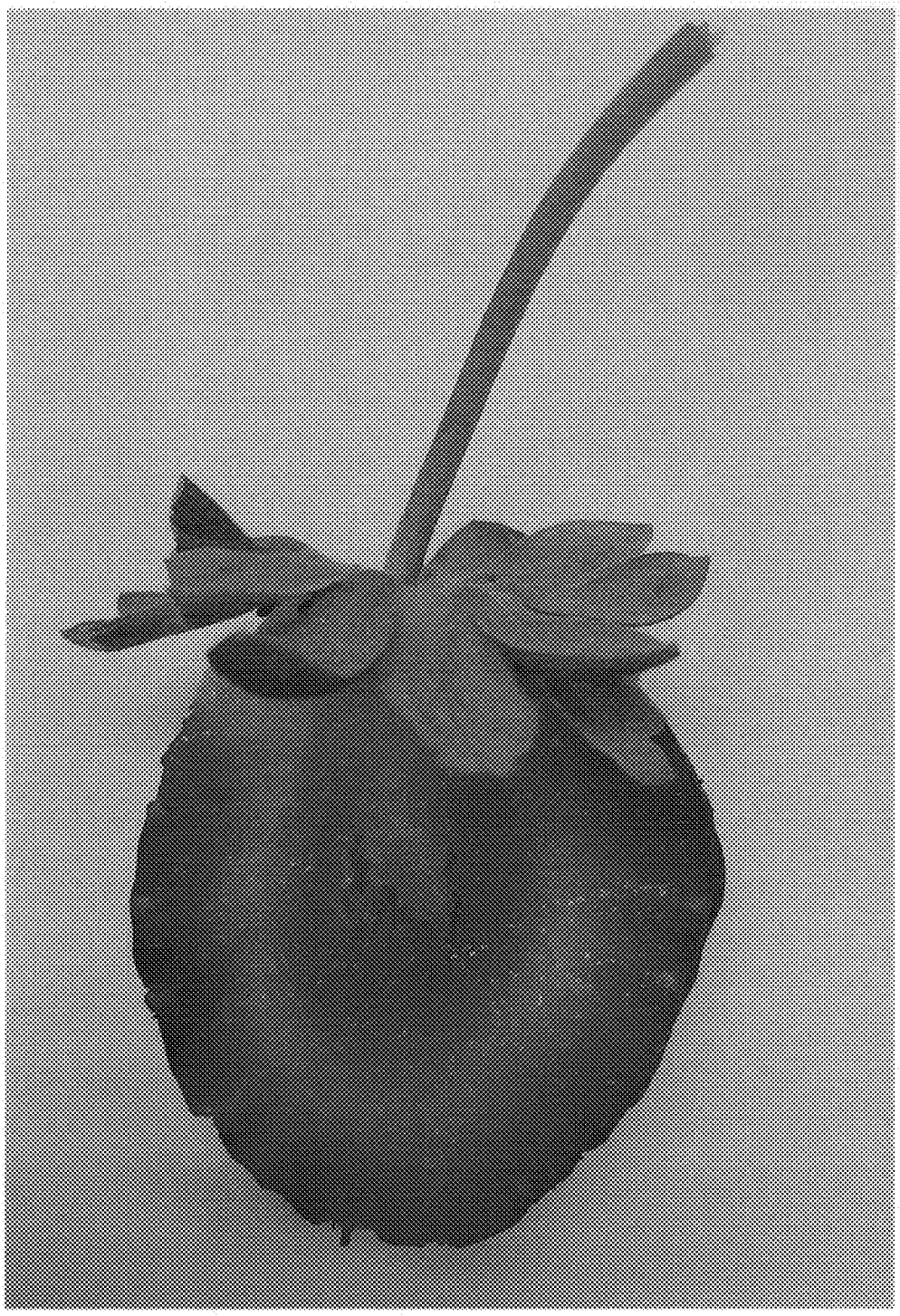
Figure 5:
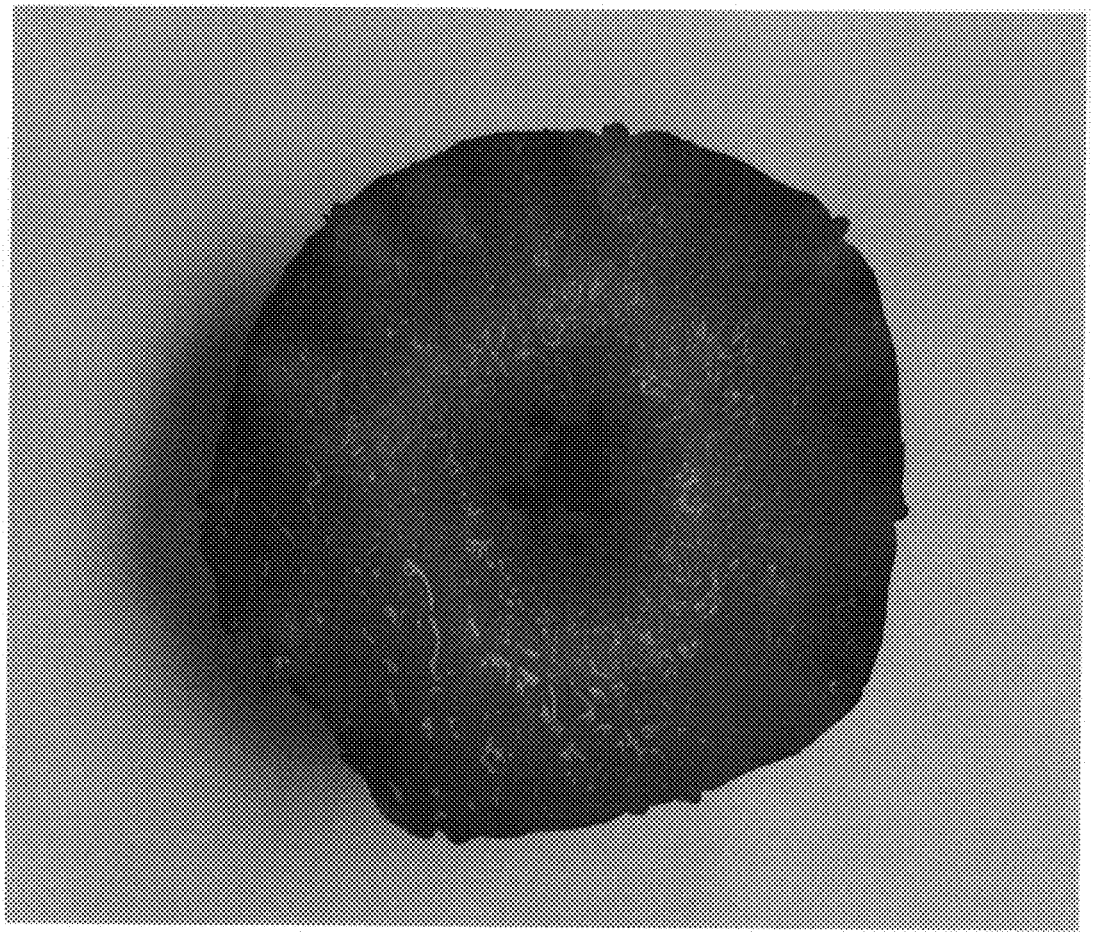

The following botanical description is that of plants of the claimed variety grown under the ecological conditions (warm days, cool nights) prevailing in Balm, Fla., during the winter production season. Colors are objectively described using the L*a*b* color scale with a colorimeter.

PHENOTYPIC DESCRIPTION OF *FRAGARIA* X *ANANASSA* DUCHESNE ('FLORIDA BEAUTY')

Plant:
- *Average height.*—15 cm.
- *Average width.*—25 cm.
- *Growth habit.*—Compact, semi-spreading plant that is not overly dense.
- *Number of crowns/plant.*—4 to 7 depending on seasonal conditions.
- *Vigor.*—Low to Medium.

Leaf:
- *Overall description.*—Pinnately compound with three leaflets.
- *Variegation.*—Absent.

Petiole:
- *Average length.*—15.5 cm.
- *Average diameter.*—2.5 mm.
- *Pubescence.*—Light to medium.
- *Pubescence density.*—Moderate to sparse.
- *Pose of hairs.*—Perpendicular.
- *Texture.*—Smooth.
- *Anthocyanin.*—Minimal to absent.
- *Color.*—Medium-light green (L*=58.9, a*=−13.3, b*=32.1).

Petiolule:
- *Length.*—Terminal leaflet 8 mm; lateral leaflets, 5 mm.
- *Diameter.*—2 mm.

Stipule:
- *Length.*—33 mm.
- *Width.*—18 mm along base of petiole attachment.
- *Anthocyanin.*—Slight to absent.
- *Color.*—Light green (L*=58.1, a*=−17.2, b*=13.0).

Terminal leaflet:
- *Average length.*—82 mm.
- *Average breadth.*—69 mm.
- *Length/width ratio.*—1.19.
- *Shape in cross section.*—Concave.
- *Color, upper surface.*—Medium-light green (L*=33.2, a*=−11.6, b*=14.5).
- *Color, lower surface.*—Light green (L*=54.4, a*=−12.9, b*=20.2).
- *Glossiness.*—Slight gloss.
- *Base shape.*—Cuneate to slightly rounded.
- *Apex descriptor.*—Rounded.
- *Pubescence density.*—Sparse.
- *Texture.*—Moderately smooth.
- *Venation pattern.*—Pinnate.

Secondary leaflets:
- *Average length.*—78 mm.
- *Average breadth.*—80 mm.
- *Length/width ratio.*—0.96.
- *Shape in cross section.*—Concave.
- *Color, upper surface.*—Medium-light green (L*=33.7, a*=−11.7, b*=14.8).
- *Color, lower surface.*—Light green (L*=54.4, a*=−12.9, b*=20.2).
- *Glossiness.*—Slight gloss.
- *Base shape.*—Oblique rounded.
- *Apex descriptor.*—Obtuse.
- *Pubescence density.*—Sparse.
- *Texture.*—Moderately smooth.
- *Venation pattern.*—Pinnate.

Leaflet margins: Crenate, with an average of 22 serrations per terminal leaflet and 22 per secondary leaflet.

Stolons:
- *Number of daughter plants.*—20-30 depending on environmental conditions.
- *Anthocyanin.*—Variable; light to moderate.
- *Thickness.*—2-3 mm.
- *Pubescence.*—Light to moderate.
- *Anthocyanin.*—Present.
- *Color.*—Light green with occasional anthocyanin (L*=47.2, a*=−13.7, b*=24.7).

Inflorescence:
- *Time of flowering.*—Full remontancy.
- *Position relative to canopy.*—Flowers open at or below canopy height.
- *Branching of the inflorescence.*—At or very close to the crown.
- *Number of sepals per flower.*—8-16.

Petals:
- *Number.*—5 to 6.
- *Length.*—12 mm.
- *Width.*—12 mm.

*Mean diameter of the corolla* (*i.e. the petals collectively*).—23.3 mm.

*Number of stamens*.—Average of 23.

*Flower arrangement of petals*.—Free.

*Color, upper surface*.—White (L*=88.3, a*=−1.2, b*=5.3).

*Color, lower surface*.—White (L*=83.4, a*=−1.2, b*=6.3).

Calyx:

*Diameter of calyx relative to corolla*.—The diameter of the calyx is 25% greater than the diameter of the corolla.

*Color*.—Medium green (L*=44.8, a*=−16.1, b*=26.5).

*Position of attachment*.—Raised.

*Diameter*.—23-51 mm.

*Level of adherence*.—Strong.

Pedicels:

*Attached to mature primary fruit*.—9.5 to 13 cm long depending on time of season. At peak production, the plant will have several crowns, each producing a truss, and each truss will have 3-7 pedicels.

*Color*.—Medium green (L*=44.4, a*=−12.8, b*=23.8).

Peduncle: Inflorescences branch very close to the crown, rendering the peduncle rarely visible.

*Anthocyanin*.—Present.

Fruit:

*Mean fruit weight*.—Slightly less than 'Florida Radiance' (Table 1).

*Shape*.—Medium conical to cordate in shape.

*Diameter*.—24-42 mm.

*Weight, primary fruit*.—27-37 g.

*Weight, secondary and tertiary fruit*.—10-23 g.

*Fruit flavor*.—Usually sweeter than 'Florida Radiance' and having strawberry flavor never lower than 'Florida Radiance' and usually not different from 'Florida127' which is the current commercial flavor standard in Florida (Table 2).

*Soluble solids content*.—10.3% (Harvested February, 2015, Balm, Fla.).

*Titratable acidity*.—0.95% (Harvested February, 2015, Balm, Fla.).

*Fruit cavity*.—Rare.

*Fruit core color*.—Light to medium red (L*=31.8, a*=30.9, b*=23.7).

*Achenes*.—Slightly sunken, giving the fruit a smooth appearance.

*Number of achenes per fruit*.—90-280.

*Achene weight*.—0.78 mg.

*Width of the band without achenes*.—5-12 mm.

*External fruit color*.—Glossy red (a*=39.1).

*Internal fruit color*.—Medium red (a*=17.4).

*Evenness of color*.—Consistently even.

*Flesh and skin firmness at full ripe stage*.—Moderately firm.

*Rain damage*.—More resistant to cracking of the fruit by rain than 'Florida127' and similar to 'Florida Radiance'.

*Difference in shape between primary and secondary fruit*.—Conic to globose.

Total yield: Not different from 'Florida127' in 2015-16 (a season with above-average temperatures, to which 'Florida Beauty' is best adapted at typical planting dates) but lower than 'Florida127' and 'Florida Radiance' in 2014-15 (a cooler season) (Table 1).

Preferred planting period: September 25$^{th}$ to October 5$^{th}$ in west-central Florida.

Nursery performance: 'Florida Beauty' is expected to perform well in nursery situations due to the production of a moderate number of runners, which result in sturdy, compact daughter plants. This is in contrast to 'Florida Radiance', whose daughter plants have weak petioles that are susceptible to breakage during digging and handling.

Disease resistance: 'Florida Beauty' is moderately susceptible to *Botrytis* fruit rot (caused by *Botrytis cinerea*), similar to 'Florida Radiance'. 'Florida Beauty' is moderately resistant to anthracnose fruit rot (caused by *Colletotrichum acutatum*).

TABLE 1

Performance of three strawberry genotypes during the 2014-15 and 2015-16 seasons in Balm, Florida

| Cultivar | Marketable yield (g/plant) November | December | January | February |
|---|---|---|---|---|
| | 2014-15 | | | |
| F. Beauty | 7.4 a | 55.5 b | 149.0 b | 180.4 b |
| Florida127 | 0.0 b | 95.8 a | 212.7 a | 288.4 a |
| F. Radiance | 1.6 b | 60.5 b | 152.2 b | 327.0 a |
| | 2015-16 | | | |
| F. Beauty | 39.6 a[y] | 87.5 a | 68.9 a | 187.7 a |
| Florida127 | 16.7 b | 75.3 a | 38.2 b | 139.4 a |

| Cultivar | Marketable yield (g/plant) March | Total | Wt/fruit (g)[z] |
|---|---|---|---|
| | 2014-15 | | |
| F. Beauty | 209.6 a | 601.3 b | 22.3 c |
| Florida127 | 206.6 a | 803.6 a | 30.8 a |
| F. Radiance | 210.9 a | 749.7 a | 25.0 b |
| | 2015-16 | | |
| F. Beauty | 129.3 a | 490.2 a | 18.9 b |
| Florida127 | 129.4 a | 411.9 a | 21.5 a |

[z]Mean fruit weight was determined by dividing total marketable fruit yield per plot by total marketable fruit number per plot.

[y]Means are based on four replications of 10 plants each in 2014-15 and on five replications of 10 plants each in the other seasons. Means separation within columns is by Tukey's HSD test, $P < 0.05$. Plants of 'Florida Radiance' were not available for the 2015-16 trial

TABLE 2

Trained sensory panel ratings from five dates over two harvest seasons

| Cultivar | Firmness | Sweetness | Sourness | Strawberry flavor | Green flavor |
|---|---|---|---|---|---|
| | January 2015 | | | | |
| F. Beauty | 5.7 a[z] | 5.9 a | 4.5 a | 5.1 a | 1.8 a |
| Florida127 | 5.6 a | 5.2 a | 4.7 a | 4.4 a | 1.8 a |
| F. Radiance | 4.9 a | 4.9 a | 4.5 a | 4.1 a | 1.6 a |
| | February 2015 | | | | |
| F. Beauty | 6.6 a | 5.2 a | 4.8 a | 4.3 ab | 2.6 a |
| Florida127 | 5.5 a | 5.4 a | 4.2 a | 4.8 a | 1.9 a |
| F. Radiance | 5.6 a | 3.9 b | 5.0 a | 3.6 b | 2.4 a |
| | March 2015 | | | | |
| F. Beauty | 3.6 b | 4.3 a | 4.5 a | 3.9 a | 1.8 a |
| Florida127 | 4.5 b | 5.0 a | 4.5 a | 4.3 a | 1.8 a |
| F. Radiance | 5.6 a | 3.1 b | 4.7 a | 3.0 b | 2.5 a |
| | February 2016 | | | | |
| F. Beauty | 5.1 a | 5.4 a | 5.4 a | 4.1 a | 2.2 a |
| Florida127 | 4.7 ab | 5.2 a | 4.8 a | 4.1 a | 2.1 a |
| F. Radiance | 4.0 b | 4.8 a | 5.4 a | 4.1 a | 2.2 a |

TABLE 2-continued

| Trained sensory panel ratings from five dates over two harvest seasons | | | | | |
|---|---|---|---|---|---|
| Cultivar | Firm-ness | Sweet-ness | Sour-ness | Straw-berry flavor | Green flavor |
| March 2016 | | | | | |
| F. Beauty | 5.3 a | 3.9 a | 6.3 a | 3.8 a | 2.6 b |
| Florida127 | 5.4 a | 4.7 a | 5.0 b | 3.6 a | 2.0 b |
| F. Radiance | 5.9 a | 2.8 b | 6.9 a | 2.0 b | 4.0 a |

[z]Mean separations are within harvest dates and within columns by Tukey's HSD test, $P \leq 0.05$.

The invention claimed is:

1. A new and distinct strawberry plant as illustrated and described herein, characterized by: (1) a compact growth habit; (2) steady yield; and (3) fruit that are exceptionally and consistently well-shaped, bright red in color and having an exceptional, balanced flavor when grown in west central Florida.

* * * * *